United States Patent [19]

Soler

[11] Patent Number: 4,727,080

[45] Date of Patent: *  Feb. 23, 1988

[54] 1-SUBSTITUTED DERIVATIVES OF 6-FLUORO-7-(PYRROL-1-YL)-1,4-DIHYDRO-4-OXOQUINOLINE-3-CARBOXYLIC ACID, THEIR PREPARATION AND THEIR APPLICATION AS DRUGS

[75] Inventor: José E. Soler, Barcelone, Spain

[73] Assignee: Provesan S.A., Genova, Switzerland

[ * ] Notice: The portion of the term of this patent subsequent to Mar. 24, 2004 has been disclaimed.

[21] Appl. No.: 806,695

[22] Filed: Dec. 9, 1985

[30] Foreign Application Priority Data

Dec. 12, 1984 [FR] France ................ 84 19001

[51] Int. Cl.⁴ .............. A61K 31/47; C07D 215/56; C07D 215/58
[52] U.S. Cl. .................... 514/312; 546/156
[58] Field of Search ................ 546/156; 514/312

[56] References Cited

U.S. PATENT DOCUMENTS

| | | | |
|---|---|---|---|
| 4,292,317 | 9/1981 | Pesson | 514/253 |
| 4,398,029 | 8/1983 | Irikura et al. | 544/363 |
| 4,499,091 | 2/1985 | Wentland et al. | 514/254 |
| 4,552,882 | 11/1985 | Esteve-Soler | 514/300 |
| 4,563,459 | 1/1986 | Grohe et al. | 514/254 |
| 4,571,396 | 2/1986 | Hutt et al. | 514/249 |
| 4,636,506 | 1/1987 | Gilligan et al. | 514/256 |

FOREIGN PATENT DOCUMENTS

0155244  9/1985  European Pat. Off. ............ 514/312

OTHER PUBLICATIONS

Artico et al., Il Farmaco, Ed. Sci., vol. 39, No. 11, pp. 910-924 (Nov. 1984).

Stefancich et al., Chemical Abstracts, vol. 102, 218189q (06/24/85).

Artico et al., Chemical Abstracts, vol. 102, p. 386, No. 21077v (1985).

*Primary Examiner*—Donald G. Daus
*Assistant Examiner*—Diana G. Rivers
*Attorney, Agent, or Firm*—Fulbright & Jaworski

[57] ABSTRACT

The present invention relates to new 1-substituted derivatives of 6-fluoro-7-(pyrrol-1-yl)-1,4-dihydro-4-oxoquinoline-3-carboxylic acid, their preparation and their application as drugs.

The 1-substituted derivatives of 6-fluoro-7-(pyrrol-1-yl)-1,4-dihydro-4-oxoquinoline-3-carboxylic acid according to the invention correspond to the general formula I:

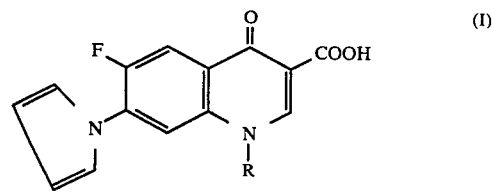

in which: R represents a methyl radical, a 2-hydroxyethyl radical, a vinyl radical, a cyclopropylmethyl radical, a propyl radical, a cyclopropyl radical, a 2-fluoroethyl radical, a methylamino radical or an ethylamino radical, as well as their physiologically acceptable alkali metal or alkaline earth metal salts.

They are useful as antimicrobial agents, in particular as antibacterial and fungistatic agents.

13 Claims, No Drawings

1-SUBSTITUTED DERIVATIVES OF 6-FLUORO-7-(PYRROL-1-YL)-1,4-DIHYDRO-4-OXOQUINOLINE-3-CARBOXYLIC ACID, THEIR PREPARATION AND THEIR APPLICATION AS DRUGS

FIELD OF THE INVENTION

The present invention relates to new 1-substituted derivatives of 6-fluoro-7-(pyrrol-1-yl)-1,4-dihydro-4-oxoquinoline-3-carboxylic acid and also to their preparation and their application as drugs.

SUMMARY OF THE INVENTION

The new derivatives forming the subject of the present invention correspond to the general formula I:

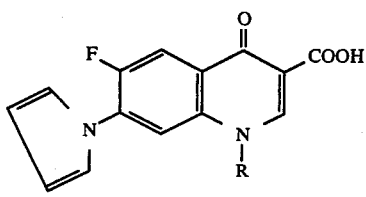

in which: R represents a methyl radical, a 2-hydroxyethyl radical, a vinyl radical, a cyclopropylmethyl radical, a propyl radical, a cyclopropyl radical, a 2-fluoroethyl radical, a methylamino radical, an ethylamino radical or an acyridyl radical.

The present invention also relates to the physiologically acceptable alkali metal or alkaline earth metal salts of the compounds of the general formula I.

The derivatives of the general formula I and their salts possess valuable antimicrobial pharmacological properties, in particular antibacterial and fungistatic properties.

The new compounds have a powerful antibacterial action towards both Gram-positive bacteria and Gram-negative bacteria.

DETAILED DESCRIPTION OF PREFERRED EMBODIMENTS

According to the invention, the new derivatives of the general formula I can be prepared in accordance with the following reaction scheme:

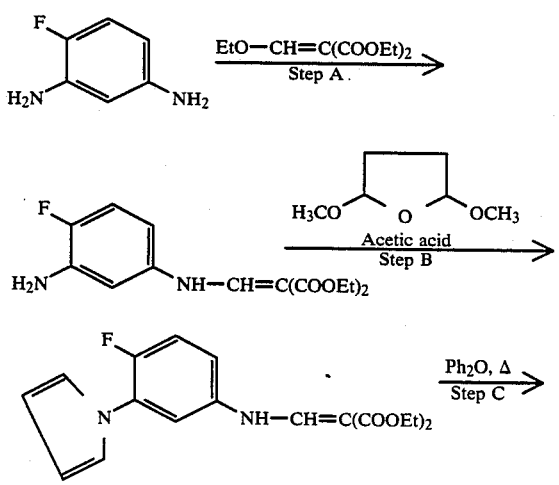

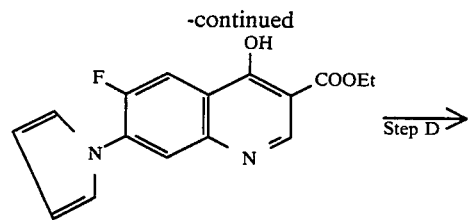

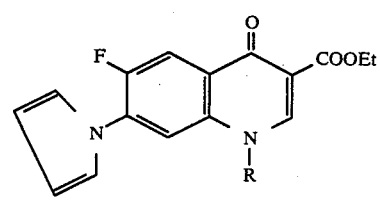

DMF, CO$_3$K$_2$
Alkyl halide

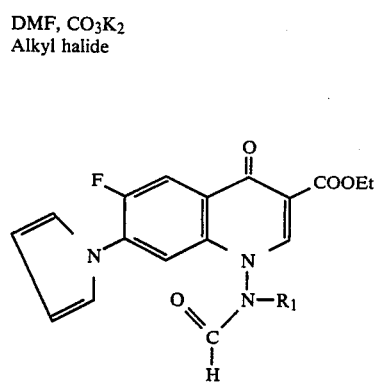

(1) N—amination
(2) Formylation
(3) DMF, CO$_3$K$_2$
 Alkyl halide in which R$_1$ represents a methyl radical or an ethyl radical.

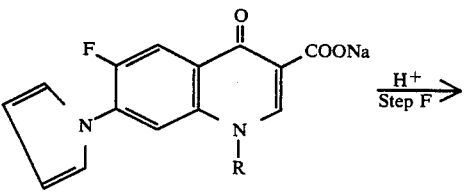

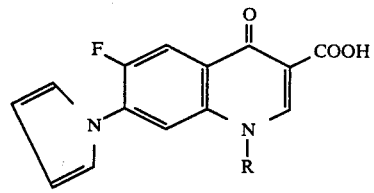

in which R has the meaning given above.

In step A, the corresponding diamine is condensed directly with diethyl ethoxymethylenemalonate to give diethyl 3-amino-4-fluoroanilinemethylenemalonate with the elimination of alcohol. In step B, the pyrrole nucleus is attached according to the method of Clauson-Kaas, Acta Chem. Scand. 6, 667 and 867 (1952), by reaction of the amine with dimethoxytetrahydrofuran under reflux in an acetic acid medium. In step C, the compound is cyclized to give the corresponding quinoline by heating either in the absence of a solvent or using a suitable solvent to act as a heat exchanger, for example benzene, toluene, xylene, tetralin, nitrobenzene, dichlorobenzene, diphenyl ether or biphenyl, or alternatively a mixture of these solvents.

The reaction temperature is between 150° C. and 250° C., preferably between 180° and 230° C.. The use of certain catalysts makes it possible to perform the cyclization at much lower temperatures. Examples of suitable catalysts which may be mentioned are polyphosphoric acid ester, polyphosphoric acid, phosphorus pentoxide, etc. The temperatures used with these catalysts are generally between 60° and 170° C. and preferably between 75° C. and 150° C.

The N-alkylated compounds are then prepared in step D. The alkylation can be carried out using one of the conventional alkylating agents, which include, inter alia, alkyl halides, halogenoalkyl halide, dialkyl sulfates, alkyl sulfonates, alkyl toluenesulfonates, etc.

In general, the reaction takes place in the presence of an alkali and in a solvent which is inert under the reaction conditions. The solvents can consist in particular of water, methanol, ethanol, acetone, dioxane, benzene, dimethylformamide or dimethyl sulfoxide, as well as mixtures of these solvents.

The preferred alkalis which can be used are alkali metal hydroxides such as sodium hydroxide or potassium hydroxide, or alternatively alkali metal carbonates such as sodium carbonate or potassium carbonate. A preferred alkylation method, which takes place in a totally anhydrous medium, uses dimethylformamide as the solvent and potassium carbonate as the alkalizing agent. The reaction temperatures are generally between 60° C. and 90° C.

In the particular case of the preparation of 6-fluoro-7-(pyrrol-1-yl)-1-methylamino-1,4-dihydro-4-oxoquinoline-3-carboxylic acid and 6-fluoro-7-pyrrol-1-yl)-1-ethylamino-1,4-dihydro-4-oxoquinoline-3-carboxylic acid, and alkylation must be preceded by N-amination with an N-aminating reagent, for example O-hydroxylaminosulfonic acid, O-mesitylenesulfonylhydroxylamine, diphenylphosphynylhydroxylamine or 2,4-dinitrophenylhydroxylamine, and then activation of the resulting amine by means of a formylation process. In step E, the ester is hydrolyzed by reaction with a 10% solution of sodium hydroxide for 3-4 hours at a temperature of 80°-90° C. In the final step F, the solution obtained in step D is acidified with hydrochloric acid or acetic acid to give the compounds forming the subject of the present invention.

The examples which follow will indicate the preparation of new derivatives according to the invention and also of the corresponding starting materials and the intermediates. A few typical use forms for the various areas of application will also be described.

The examples below, which are given simply by way of illustration, must not however in any way restrict the scope of the invention.

EXAMPLE 1

Preparation of diethyl 4-fluoro-3-aminoanilinemethylenemalonate (step A)

10.8 grams of 4-fluoro-m-phenylenediamine are dissolved in 80 ml of ethyl alcohol, 21.6 grams of diethyl ethoxymethylenemalonate are added and the mixture is heated under reflux for 40 minutes. It is filtered hot, 50 ml of water are added and the mixture is left at room temperature for 24 to 36 hours, with stirring. The precipitate formed is filtered off, washed with an ethanol/water mixture (1:1) and dried at 60° C. It is recrystallized from a benzene/hexane mixture (2:1) to give 10.5 grams of a solid melting at 71°-74° C.

Preparation of diethyl 3-pyrrole-4-fluoroanilinemethylenemalonate (step B)

1.48 g (0.005 mol) of diethyl 4-fluoro-3-aminoanilinemethylenemalonate are dissolved in 10 ml of glacial acetic acid, and 0.66 g (0.005 mol) of dimethoxytetrahydrofuran is added. The mixture is heated at the boil for 3-4 minutes, 5 ml of water are added and the resulting mixture is left to cool. The precipitate formed is filtered off and washed with water. It is recrystallized from an ethanol/water mixture (1:1) to give 1.5 g of a solid melting at 82°-83° C.

Preparation of ethyl 6-fluoro-7-(pyrrol-1-yl)-4-hydroxyquinoline-3-carboxylate (step C)

2.5 g of diethyl 3-pyrrole-4-fluoroanilinemethylenemalonate are suspended in 10 ml of diphenyl ether under a nitrogen atmosphere and the suspension is heated to 250° C., kept at the boil for 5 minutes and left to cool. The precipitate formed is filtered off and washed wtih benzene and then washed with ethanol. The precipitate is dried and treated with acetic acid at the boil to remove the impurities, the mixture is filtered hot and the precipitate is washed with acetic acid and then with ethanol to give 1.2 g of a solid melting at 316°-318° C.

Preparation of ethyl 6-fluoro-7-(pyrrol-1-yl)-1-methyl-1,4-dihydro-4-oxoquinoline-3-carboxylate (step D)

A mixture of 1.5 g (0.005 mol) of ethyl 6-fluoro-7-(pyrrol-1-yl)-4-hydroxyquinoline-3-carboxylate and 1.4 g (0.01 mol) of potassium carbonate in 10 ml of dimethylformamide is heated for 30 minutes at 60° C. and left to cool, 2.15 g (3×0.005 mol) of methyl iodide are added, the mixture is heated at 80°-90° C. for 4 hours and left to cool, 25 ml of a water/ice mixture are added and the precipitate formed is filtered off and washed with water. The precipitate is receystallized from ethanol to give 1.2 g of a solid melting at 253°-254° C.

Preparation of 6-fluoro-7-(pyrrol-1-yl)-1-methyl-4-oxo-1,4-dihydroquinoline-3-carboxylic acid (steps E and F)

A mixture of 1.2 g of ethyl 6-fluoro-7-(pyrrol-1-yl)-1-methyl-1,4-dihydro-4-oxoquinoline-3-carboxylate, 10 ml of ethanol, 15 ml of 10% sodium hydroxide solution and 10 ml of water is heated under reflux for 2 hours. 30 ml of 8M hydrochloric acid are added, the mixture is left to cool and the product is filtered off, washed with water and recrystallized from acetic acid to give 0.75 g of a solid melting at 284°-285° C.

Spectroscopic data $^1$H NMR, δ [DMSO (d$_6$)]: 3.48 (s, 3H); 5.74 (m, 2H); 6.74 (m, 2H); 7.31 [d (J$_{HF}$: 7 Hz), 1H]; 7.43 [d (J$_{HF}$: 13 Hz), 1H]; 8.28 (s, 1H); 14.0 (b, 1H).

IR (KBr): 1475, 1620, 1725 cm$^{-1}$.

EXAMPLE 2

Preparation of ethyl 6-fluoro-7-(pyrrol-1-yl)-1-(2-hydroxyethyl)-4-oxo-1,4-dihydroquinoline-3-carboxylate (step D)

A mixture of 2 g (0.0076 mol) of ethyl 6-fluoro-7-(pyrrol-1-yl)-4-hydroxyquinoline-3-caboxylate and 1.85 g (2×0.0076 mol) of potassium carbonate in 20 ml of dimethylformamide is heated for 30 minutes at 60° C. and left to cool, 3.35 g (4×0.0076 mol) of ethylene bromohydrin are added, the mixture is heated at 80°–90° C. for 10 hours, active carbon is added, the mixture is filtered hot, the filtrate is evaporated to dryness, water is added and the precipitate formed is filtered off and washed with water. It is recrystallized from dimethylformamide to give 1.2 g of a solid melting at 237°–239° C.

Preparation of 6-fluoro-7-(pyrrol-1-yl)-1-(2-hydroxyethyl)-4-oxo-1,4-dihydroquinoline-3-carboxylic acid (steps E and F)

A mixture of 5 g of ethyl 6-fluoro-7-(pyrrol-1-yl)-1-(2-hydroxyethyl)-4-oxo-1,4-dihydroquinoline-3-carboxylate, 20 ml of 10% sodium hydroxide solution, 20 ml of ethanol and 35 ml of water is heated under reflux for 3 hours. It is acidified hot with hydrochloric acid, left to cool and filtered, and the product is washed with water and recrystallized from dimethylformamide to give 3.6 g of a solid melting at 230° C.

Spectroscopic data: $^1$H NMR, $\delta$ [DMSO (d$_6$)]: 3.16 (m, 2H); 4.0 (t, 2H); 4.37 (t, 1H); 5.74 (m, 2H); 6.72 (m, 2H); 7.46 [d ($J_{HF}$: 6 Hz), 1H]; 7.48 [d ($J_{HF}$: 12 Hz), 1H]; 8.23 (s, 1H); 14.0 (b, 1H).

IR (KBr): 1620, 1700, 3400 cm$^{-1}$.

EXAMPLE 3

Preparation of ethyl 6-fluoro-7-(pyrrol-1-yl)-1-(2-chloroethyl)-4-oxo-1,4-dihydroquinoline-3-carboxylate 3.5 g (0.01 mol) of ethyl 6-fluoro-7-(pyrrol-1-yl)-1-(2-hydroxyethyl)-4-oxo-1,4-dihydroquinoline-3-carboxylate are suspended in 30 ml chloroform, 3 ml of Cl$_3$PO are added, the mixture is kept at room temperature for 2 hours and evaporated to dryness, the residue is redissolved in chloroform, the resulting solution is washed with a sodium bicarbonate solution and then with water and evaporated, and the precipitate is recrystallized from dimethylformamide to give 3.3 g of a solid melting at 254°–256° C.

Preparation of 6-fluoro-7-(pyrrol-1-yl)-1-vinyl-4-oxo-1,4-dihydroquinoline-3-carboxylic acid (steps E and F)

A mixture of 3.3 g (0.01 mol) of ethyl 6-fluoro-7-(pyrrol-1-yl)-1-(2-chloroethyl)-4-oxo-1,4-dihydroquinoline-3-carboxylate and a solution of 4 g (0.01 mol) of sodium hydroxide in 40 ml of water and 20 ml of ethanol is kept under reflux for 5 hours. Part of the ethanol is evaporated off, the residue is acidified hot with hydrochloric acid and the product is filtered off, washed with water, left to cool and recrystallized from dimethylformamide to give 1.7 g of a solid melting at 252°–254° C.

Spectroscopic data: $^1$H NMR, $\delta$ [DMSO (d$_6$)]: 5.68 (dd, 1H); 5.95 (dd, 1H); 6.40 (m, 2H); 7.3 (m, 2H); 7.65 (dd, 1H); 7.95 [d ($J_{HF}$: 6.3 Hz), 1]; 8.10 [d ($J_{HF}$: 12 Hz), 1H]; 8.80 (s, 1H); 15.0 (b, 1H).

IR (KBr): 1610, 1720 cm$^{-1}$.

EXAMPLE 4

Preparation of ethyl 6-fluoro-7-(pyrrol-1-yl)-1-cyclopropylmethyl-4-oxo-1,4-dihydroquinoline-3-carboxylate (step D)

A mixture of 3.6 g (0.012 mol) of ethyl 6-fluoro-7-(pyrrol-1-yl)-4-hydroxyquinoline-3-carboxylate and 4.15 g (0.03 mol) of potassium carbonate in 30 ml of dimethlformamide is heated for 30 minutes at 80° C. and left to cool, 8 g (0.06 mol) of cyclopropylmethyl bromide are added, the mixture is kept for 12 hours at 90° C. and left to cool, 80 ml of a water/ice mixture are added and the precipitate formed is filtered off, washed with water and recrystallized from ethanol to give 2.65 g of a solid melting at 125°–127° C.

Preparation of 6-fluoro-7-(pyrrol-1-yl)-1-cyclopropylmethyl-4-oxo-1,4-dihydroquinoline-3-carboxylic acid (steps E and F)

A mixture of 2.65 g of ethyl 6-fluoro-7-(pyrrol-1-yl)-1-cyclopropylmethyl-4-oxo-1,4-dihydroquinoline-3-carboxylate, 10 ml of 10% sodium hydroxide solution, 30 ml of water and 15 ml of ethanol is kept under reflux for 2 hours. It is acidified hot with dilute acetic acid and left to cool, and the precipitate formed is filtered off, washed with water and recrystallized from acetonitrile to give 1.8 g of a solid melting at 228°–230° C.

Spectroscopic data: $^1$H NMR, $\delta$ [DMSO (d$_6$)]: 0.4–0.8 (m, 4H); 1.2–1.6 (m, 1H); 4.50 (d, 2H); 6.3 (m, 2H); 7.35 (m, 2H); 8.02 [d ($J_{HF}$: 12 Hz), 1H]; 8.08 [d ($J_{HF}$: 7 Hz), 1H]; 8.9 (s, 1H); 14.7 (s, 1H).

IR (KBr): 1620, 1725 cm$^{-1}$.

EXAMPLE 5

Preparation of ethyl 6-fluoro-7-(pyrrol-1-yl)-1-propyl-4-oxo-1,4-dihydroquinoline-3-carboxylate (step D)

A mixture of 3 g (0.01 mol) of ethyl 6-fluoro-7-(pyrrol-1-yl)-4-hydroxyquinoline-3-carboxylate, 2.8 g (0.02 mol) of potassium carbonate and 6 g (0.04 mol) of n-propyl bromide is heated for 5 hours at 80°–90° C. and left to cool, water is added and the precipitate formed is filtered off, washed with water and recrystallized from ethanol to give 2.4 g of a solid melting at 128°–130° C.

Preparation of 6-fluoro-7-(pyrrol-1-yl)-1-propyl-4-oxo-1,4-dihydroquinoline-3-carboxylic acid (steps E and F)

A mixture of 2.4 g of ethyl 6-fluoro-7-(pyrrol-1-yl)-1-propyl-4-oxo-1,4-dihydroquinoline-3-carboxylate, 10 ml of 10% sodium hydroxide solution, 30 ml of water and 15 ml of ethanol is kept under reflux for 3 hours. It is acidified hot with hydrochloric acid and the precipitate formed is filtered off, washed with water and recrystallized from acetonitrile to give 1.6 g of a solid melting at 217°–219° C.

Spectroscopic data: $^1$H NMR, $\delta$ [DMSO (d$_6$)]: 1.0 (t, 3H); 1.85 (m, 2H); 4.6 (t, 2H); 6.3 (m, 2H); 7.2 (m, 2H); 7.97 [d ($J_{HF}$: 6 Hz), 1H]; 7.97 [d ($J_{HF}$: 12 Hz), 1H]; 8.8 (s, 1H); 14.7 (s, 1H).

IR (KBr): 1620, 1720 cm$^{-1}$.

EXAMPLE 6

Preparation of ethyl 6-fluoro-7-(pyrrol-1-yl)-1-fluoroethyl-4-oxo-1,4-dihydroquinoline-3-carboxylate (step D)

A mixture of 3.2 g (0.011 mol) of ethyl 6-fluoro-7-(pyrrol-1-yl)-4-hydroxyquinoline-3-carboxylate and 4 g (2.5×0.011 mol) of potassium carbonate in 20 ml of dimethylformamide is heated for 30 minutes at 60° C. and left to cool, 7 g (5×0.011 mol) of bromofluoroethane are added, the mixture is kept for 7 hours at 80° C., left to cool and poured into a water/ice mixture, and the precipitate formed is filtered off, washed with water and recrystallized from a dimethylformamide/water mixture (1:1) to give 2.35 g of a solid melting at 231°–234° C.

Preparation of 6-fluoro-7-(pyrrol-1-yl)-1-fluoroethyl-4-oxo-1,4-dihydroquinoline-3-carboxylate acid (steps E and F)

A mixture of 0.9 g of ethyl 6-fluoro-7-(pyrrol-1-yl)-1-fluoroethyl-4-oxo-1,4-dihydroquinoline-3-caboxylate, 15 ml of water, 15 ml of concentrated hydrochloric acid and 15 ml of ethanol is kept under reflux for 2.5 hours, and the precipitate formed is left to cool, filtered off, washed with water and recrystallized from acetic acid to give 0.3 g of a solid melting at 251°–254° C.

Spectroscopic data: $^1$H NMR, δ [DMSO (d$_6$)]: 5.0–5.8 (m, 4H); 6.9 (m, 2H); 7.9 (m, 2H); 8.64 [d ($J_{HF}$: 6 Hz), 1H]; 8.71 [d ($J_{HF}$: 12 Hz), 1H]; 9.5 (s, 1H); 13.9 (b, 1H).

IR (KBr): 1620, 1715 cm$^{-1}$.

EXAMPLE 7

Preparation of ethyl 6-fluoro-7-(pyrrol-1-yl)-1-amino-4-oxo-1,4-dihydroquinoline-3-carboxylate (step D-1)

A mixture of 6 g (0.02 mol) of ethyl 6-fluoro-7-(pyrrol-1-yl)-4-hydroxyquinoline-3-carboxylate and 5.6 g (0.04 mol) of potassium carbonate in 80 ml of dimethylformamide is heated for 30 minutes at 60° C. and left to cool, 8.5 g (0.042 mol) of 2,4-dinitrophenylhydroxylamine are added, the mixture is kept for 24 hours at room temperature and poured into 200 ml of a water/ice mixture, and the precipitate formed is filtered off, washed with water, dried in a desiccator and recrystallized from dimethylformamide to give 1.5 g of a solid melting at 276°–279° C.

Preparation of ethyl 6-fluoro-7-(pyrrol-1-yl)-1-formylamino-4-oxo-1,4-dihydroquinoline-3-carboxylate (step D-2)

A solution of 3.15 g (0.01 mol) of ethyl 6-fluoro-7-(pyrrol-1-yl)-1-amino-4-oxo-1,4-dihydroquinoline-3-carboxylate in 25 ml of formic acid is added dropwise to a mixture of 9.5 ml (0.01 mol) of acetic anhydride and 4 ml (0.01 mol) of formic acid, cooled to 0° C., the addition being carried out so as to maintain room temperature ±5° C. The mixture is kept at room temperature for 48 hours and poured into a water/ice mixture, and the precipitate formed is filtered off, washed with water and recrystallized from a dimethylformamide/water mixture (1:1) to give a solid melting at 254°–257° C.

Preparation of ethyl 6-fluoro-7-(pyrrol-1-yl)-1-formylmethylamino-4-oxo-1,4-dihydroquinoline-3-carboxylate (step D-3)

A mixture of 3.47 g (0.01 mol) of ethyl 6-fluoro-7-(pyrrol-1-yl)-1-formylamino-4-oxo-1,4-dihydroquinoline-3-carboxylate and 3 g (~0.02 mol) of potassium carbonate in 25 ml of dimethylformamide is heated for 10 minutes at 35° C. It is kept at room temperature for 2 hours in a partially precipitated state, 4.3 g (0.03 mol) of methyl iodide are added to this suspension and the mixture is kept at room temperature for 3 hours. It is poured into a water/ice mixture, the precipitate formed is filtered off, washed with water and extracted with chloroform, the mixture is filtered, the solution is evaporated and the residue is recrystallized from an ethanol/water mixture (1:1) to give 1.43 g of a solid melting at 194°–198° C.

Preparation of 6-fluoro-7-(pyrrol-1-yl)-1-methylamino-4-oxo-1,4-dihydroquinoline-3-carboxylic acid (steps E and F)

A mixture of 1.43 g of ethyl 6-fluoro-7-(pyrrol-1-yl)-1-formylmethylamino-4-oxo-1,4-dihydroquinoline-3-carboxylate, 8 ml of 10% sodium hydroxide solution, 40 ml of water and 10 ml of ethanol is kept under reflux for 2 hours. The ethanol is evaporated off, the residue is acidified hot with acetic acid and left to cool, and the precipitate is filtered off, washed with water and recrystallized from a dimethylformamide/ethanol mixture (1:1) to give 1 g of a solid melting at 252°–256° C.

Spectroscopic data: $^1$H NMR, δ [DMSO (d$_6$)]: 2.8 (d, 3H); 6.3 (m, 2H); 7.1 (b, 1H); 7.25 (m, 2H); 8.05 [d $J_{HF}$: 6 Hz), 1H]; 8.15 [d ($J_{HF}$: 11 Hz), 1H]; 8.9 (s, 1H); 14.8 (s, 1H).

IR (KBr): 1615, 1710, 3290 cm$^{-1}$.

EXAMPLE 8

Preparation of ethyl 6-fluoro-7-(pyrrol-1-yl)-1-formylethylamino-4-oxo-1,4-dihydroquinoline-3-carboxylate (step D-3)

A mixture of 1.5 g (0.005 mol) of ethyl 6-fluoro-7-(pyrrol-1-yl)-1-formylamino-4-oxo-1,4-dihydroquinoline-3-carboxylate and 1.3 g (0.01 mol) of potassium carbonate in 10 ml of dimethylformamide is stirred for 3 hours at room temperature, 2.35 g (0.015 mol) of ethyl iodide are then added and the mixture is kept for 4 hours at room temperature. It is poured into a water/ice mixture, the precipitate obtained is filtered off, washed with water and extracted with chloroform, the extract is washed with water, the organic layer is dried, the solvent is evaporated off and the residue is recrystallized from an ethanol/water mixture (1:1) to give 0.7 g of a solid melting at 192°–194° C.

Preparation of 6-fluoro-7-(pyrrol-1-yl)-1-ethylamino-4-oxo-1,4-dihydroquinoline-3-carboxylic acid (steps E and F)

A mixture of 0.7 g of ethyl 6-fluoro-7-(pyrrol-1-yl)-1-formylethylamino-4-oxo-1,4-dihydroquinoline-3-carboxylate, 5 ml of 10% sodium hydroxide solution, 25 ml of water and 10 ml of ethanol is kept under reflux for 2 hours. The ethanol is evaporated off, the residue is acidifed hot with acetic acid and the precipitate formed is filtered off, washed with water and recrystallized from a dimethylformamide/ethanol mixture (1:1) to give 0.36 g ofa solid melting at 271°–274° C.

Spectroscopic data: $^1$H NMR, δ [DMSO (d$_6$)]: 1.13 (t, 3H); 3.22 (q, 2H); 6.42 (m, 2H); 7.26 (b, 1H); 7.37 (m, 2H); 8.15 [d ($J_{HF}$: 6 Hz), 1H]; 8.16 [d ($J_{HF}$: 11 Hz), 1H]9.02 (s, 1H); 14.9 (s, 1H).

IR (KBr): 1620, 1715, 3280 cm$^{-1}$.

EXAMPLE 9

Preparation of 2,5-difluoro-4-(pyrrol-1-yl)benzoic acid (step B)

5.2 grams (0.03 mol) of 2,5-difluoro-4-aminobenzoic acid, melting at 250°–3°, are dissolved in 60 ml of glacial acetic acid, and 4 grams (0.03 mol) of dimethoxytetrahydrofuran are added. The mixture is heated at the boil for 10 minutes, 20 ml of water are added and the resulting mixture is left to cool. The precipitate formed is filtered off and washed with water to give 5.3 grams of a solid melting at 196°–8° C.

Preparation of 3,5-difluoro-4-(pyrrol-1-yl)benzoic acid chloride

A mixture of 4 g (0.018 mol) of 2,5-difluoro-4-(pyrrol-1-yl)benzoic acid and 3.74 g (0.018 mol) of $PCl_5$ is heated for 10 minutes at 110° C. It is cooled to room temperature, 30 ml of chloroform are added, the solution is decolorized with carbon black and filtered and the filtrate is evaporated to dryness. The residue is recrystallized from hexane to give 3.4 g of a solid melting at 82°–5° C.

Preparation of ethyl 2,5-difluoro-4-(pyrrol-1-yl)benzoylacetate 0.39 g (0.016 mol) of magnesium filings, 0.35 ml of absolute ethanol and 0.2 ml of carbon tetrachloride are placed in a 100 ml three-necked flask (equipped with a mechanical stirrer, a dropping funnel protected by a drying tube, and a thermometer). The mixture is heated slowly until the reaction starts, stirring is continued for 15 minutes and 15 ml of anhydrous ethyl ether are added. A solution of 2.48 g (0.0155 mol) of diethyl malonate with 1.4 ml (0.024 mol) of absolute ethanol in 5 ml of anhydrous ethyl ether is added hot so as to maintain reflux. The reaction mixture is heated under reflux for 5 hours and then 3.4 g (0.0141 mol) of 2,5-difluoro-4-(pyrrol-1-yl)benzoic acid chloride in 10 ml of anhydrous ethyl ether are added. Refluxing is continued for one hour, the mixture is left to cool and 25 ml of 5% sulfuric acid are added. The 2 layers are separated, extraction is carried out with 2×10 ml of ethyl ether and the ether fractions are combined, dried with sodium sulfate and evaporated to dryness. The residue is taken up with 20 ml of a water/ethyl alcohol mixture (1:1), 0.2 g of toluenesulfonic acid is added, the mixture is refluxed for 18 hours and left to cool and extraction is carried out with 2×20 ml with ethyl ether. The ethyl ether solution is washed with a 10% sodium bicarbonate solution and water, dried with sodium sulfate and evaporated to dryness to give 1.1 g of an oily residue.

Spectroscopic data: $^1H$ NMR, $\delta$ ($CCl_4$): two classes of signals—1.2 (t, 3H, J=7 Hz); 1.3 (t, 3H, J=7 Hz); 3.15 (s, 2H); 4.1 (q, 2H, J=7 Hz); 4.15 (q, 2H, J=7 Hz); 5.7 (s, 1H); 6.2 (m, 2H); 6.9 (m, 2H); 6.95 (q, 1H, J=7 Hz); 7.0 (q, 1H, J=7 Hz); 7.50 (q, 1H, J=7 Hz); 7.55 (q, 1H, J=7 Hz); 12.6 (s, 1H, enol).

Preparation of ethyl 3-cyclopropylamino-2-(2,5-difluoro-4-pyrrol-1-ylbenzoyl)acrylate 1 g (0.0068 mol) of ethyl orthoformate is added to a solution of 1.1 g (0.00315 mol) of ethyl 2,5-difluoro-4-(pyrrol-1-yl)benzoylacetate in 3 ml of acetic anhydride and the mixture is refluxed for 3 hours. It is evaporated to dryness, the residue is dissolved in 10 ml of ethanol, 0.3 ml (0.0034 mol) of cyclopropylamine is added and the mixture is left at room temperature for 1 hour. It is evaporated to dryness and the oily residue is extracted with 3×30 ml of boiling hexane. The hexane fractions are concentrated to 20 ml and left for 12 hours at 5° C. to give 0.41 g of crystals melting at 90°–2° C.

Preparation of ethyl 6-fluoro-7-(pyrrol-1-yl)-1-cyclopropyl-1,4-dihydro-4-oxoquinoline-3-carboxylate 0.07 g (0.00115 mol) of a 60% suspension of sodium hydride in mineral oil is added to a solution of 0.41 g (0.00114 mol) of ethyl 3-cyclopropylamino-2-(2,5-difluoro-4-pyrrol-1-ylbenzoyl)acrylate in 10 ml of anhydrous dioxane. The mixture is heated at 80° C. for 2 hours under a nitrogen atmosphere and left to cool, 30 ml of water are added and the precipitate is filtered off and washed with water to give 0.3 g of a product melting at 216°–9° C.

Preparation of 6-fluoro-7-(pyrrol-1-yl)-1-cyclopropyl-1,4-dihydro-4-oxoquinoline-3-carboxylic acid (steps E and F)

0.3 g of ethyl 6-fluoro-7-(pyrrol-1-yl)-1-cyclopropyl-1,4-dihydro-4-oxoquinoline-3-carboxylate is added to a mixture of 5 ml of 10% sodium hydroxide solution, 20 ml of water and 5 ml of ethanol. The resulting mixture is refluxed for 2 hours, left to cool and acidified with 2N hydrochloric acid. The precipitate is filtered off, washed with water and dried at 60° C. The residue is recrystallized from acetonitrile to give 0.16 g of needles melting at 258°–260° C.

Spectrscopic data: $^1H$ NMR $\delta$ (DMSO-$d_6$): 1.4 (m, 4H); 4.0 (m, 1H); 6.4 (m, 2H); 7.35 (m, 2H); 8.2 (d, 1H, J=12 Hz); 8.35 (d, 1H, J=6 Hz); 8,8 (s, 1H); 14,5 (s, 1H).

IR (KBr): 1725, 1625, 1460 $cm^{-1}$.

Antimicrobial pharmacological activity (G. L. Daquet and Y. A. Chabbect, Techniques en bactériologie (Techniques in bacteriology), vol. 3, Flammarion Medecine-Sciences, Paris, 1972, and W. B. Hugo and A. D. Rusell, Pharmaceutical Microbiology, Blackwell Scientific Publications, London (1977).

Culture medium and solvent

Antibiotics agar no. 1 (Oxoid CM 327)
Tryptone-soya broth (Oxoid CM 129)
Ringer's ¼ physiological solution (Oxoid BR 52)
Dextrose agar (BBl-11165)
0.1N NaOH Microorganisms

*Bacillus subtilis* ATCC 6633
*Micrococcus flavus* ATTC 10240
*Sarcina lutea* ATTC 9341
*Staphylococcus aureus* ATCC 5488/23
*Staphylococcus aureus* ATCC 25178
*Streptococcus faecalis* ATCC 10541
*Enterobacter aerogenes* ATCC 15038
*Enterobacter cloacae* CHSP-20
*Escherichia coli* ATCC 10536
*Escherichia coil* R-1513
*Klebsiella pneumoniae* ATCC 10031
*Citrobacter freundii* ATCC 11606
*Proteus mirabilis* ATCC 4675
*Proteus morganii* CHSP-16
*Pseudomonas aeruginosa* 25115
*Pseudomonas aeruginosa* ADSA 47
*Salmonella typhimurium* AMES 98
*Salmonella typhimurium* AMES 100
*Serratia marcescens* ATTC 13880
*Shigella flexnerii*

Preparation of the inoculations

A streak culture of each of the microorganisms is formed in tubes of antibiotics agar no. 1 and incubated for 20 hours at 37° C. A culture loop is then taken and a culture is formed in a tryptone-soya broth and incubated for 20 hours at 37° C. The resulting culture is diluted to ¼ with Ringer's physiological solution to give a standardized suspension of $10^5$ ufc/ml for each organism.

Preparation of the medium containing the derivatives of the general formula I

Results

The results obtained are described in Table I. The products of Examples 2, 3, 6 and 7 have a greater "in vitro" activity than nalidixic acid with regard to both Enterobacteriaceae (*Pseudomonas aeruginosa*) and Gram-positive cocci. The derivatives of Examples 1, 4, 5 and 8 have an activity of the same order as nalidixic acid towards Gram-negative microorganisms and a greater activity towards Gram-positive cocci. The derivative of example 9 presents an activity which is greater than the activity of nalidixic acid, against all microorganisms.

TABLE I

"In vitro" MIC compared with nalidixic acid
The concentrationa are ginve in µg/ml

| MICROORGANISMS | Compound of example 1 | Compound of example 2 | Compound of example 3 | Compound of example 4 | Compound of example 5 | Compound of example 6 | Compound of example 7 | Compound of example 8 | Compound of example 9 | Nalidixic acid |
|---|---|---|---|---|---|---|---|---|---|---|
| *Bacillus subtilis* ATCC 6633 | 0.125 | ≦0.062 | ≦0.062 | 0.125 | 0.125 | ≦0.031 | ≦0.062 | ≦0.062 | 0.25 | 1 |
| *Micrococcus flavus* ATCC 10240 | 4 | 16 | 4 | 1 | 8 | 1 | 4 | 2 | 0.5 | 128 |
| *Sarcina lutea* ATCC 9341 | 16 | 16 | 8 | 8 | 8 | 2 | 4 | 4 | 0.5 | 128 |
| *Staphylococcus aureus* ATCC 5488/23 | 0.50 | 0.50 | 0.50 | 2 | 0.50 | 0.062 | 0.25 | 0.25 | <0.06 | 32 |
| *Staphylococcus aureus* ATCC 25178 | 0.50 | 0.50 | 0.50 | 1 | 0.50 | 0.062 | 0.25 | 0.25 | <0.06 | ≧64 |
| *Streptococcus faecalis* ATCC 10541 | 32 | 1 | 16 | 16 | 8 | 0.50 | 4 | 4 | 0.25 | ≧64 |
| *Enterobacter aerogenes* ATCC 15038 | 2 | 2 | 1 | 8 | 8 | 1 | 1 | 2 | 0.12 | 4 |
| *Enterobacter cloacae* CHSP-20 | 2 | 1 | 1 | 4 | 4 | 0.50 | 1 | 1 | 0.12 | 4 |
| *Escherichia coli* ATCC 10536 | 0.05 | 0.125 | 0.125 | 0.25 | 0.50 | ≦0.031 | ≦0.062 | 0.062 | <0.06 | 0.25 |
| *Escherichia coli* R-1513 | 4 | 1 | 1 | 8 | 8 | 0.50 | 0.50 | 4 | 0.12 | 4 |
| *Klebsiella pneumoniae* ATCC 10031 | 1 | 0.062 | 0.50 | 1 | 0.50 | 0.062 | 0.125 | 0.25 | <0.06 | 1 |
| *Citrobacter freundii* ATCC 11606 | 2 | 1 | 1 | 16 | 8 | 1 | 1 | 4 | 0.25 | 4 |
| *Proteus mirabilis* ATCC 4675 | 4 | 1 | 2 | 32 | 16 | 1 | 2 | 8 | 0.5 | 8 |
| *Proteus morganii* CHSP-16 | 2 | 1 | 2 | 8 | 8 | 0.50 | 1 | 4 | 0.5 | 1 |
| *Pseudomonas aeruginosa* 25115 | 16 | 16 | 4 | ≧32 | 32 | 4 | 8 | 16 | 1 | ≧128 |
| *Pseudomonas aeruginosa* ADSA 47 | ≧32 | ≧32 | 8 | ≧32 | 32 | 16 | 16 | ≧32 | 2 | ≧128 |
| *Salmonella typhimurium* AMES 98 | 4 | 0.25 | ≦0.062 | 0.25 | 1 | ≦0.031 | 0.125 | 0.062 | 1 | 0.50 |
| *Salmonella typhimurium* AMES 100 | 8 | 0.25 | 0.50 | 2 | 1 | 0.25 | 0.25 | 1 | <0.06 | 0.50 |
| *Serratia marcescens* ATTC 13880 | 16 | 1 | 1 | 4 | 1 | 1 | 1 | 2 | 0.5 | 1 |
| *Shigella flexnerii* | 4 | 1 | 1 | 4 | 4 | 1 | 1 | 1 | 0.2 | 2 |

Starting from a solution of 1000 µg/ml in 0.1N NaOH, each product is diluted successively in dextrose agar (melted beforehand and kept at 50° C.) to give the following concentrations: 64-32-16-8-4-2-1-0.5-0.25-0.125 µg of derivative/ml of medium.

After this, each concentration of each product is divided up into Petri dishes of 10 cm diameter at a rate of 10 ml of medium per dish and using as many dishes as there are microorganisms to be tested.

Once the medium has cooled, the dishes are treated with the inoculations at a rate of 0.4 ml of inoculation per dish. They are spread out with a Drigalski loop and the supernatant is collected. The inoculated dishes are incubated at 37° C. for 20 hours.

Acute toxicity to mice

The experimental animals used to determine this toxicity were albino mice of the C.F.L.P. strain and of both sexes, weighing between 19 and 25 grams. After an 18-hour fasting period with water "ad libitum", the derivatives forming the subject of the present invention are administered intraperitoneally as a suspension in 5% gum arabic. The volume of suspension administered was 0.4 ml/20 grams (20 ml/kg) in all cases, the concentration of the suspension being changed according to the dose administered.

One hour after administration of the derivatives, the animals are given a standard Panlab rat-mouse food. The mortality was observed over a period of 7 days.

Differences in mortality between the sexes were not observed with any of the products.

The results obtained as described in Table II.

TABLE II

| Derivative | Method of administration | LD$_{50}$ mg/kg |
|---|---|---|
| Example 1 | i.p. | >800 |
| Example 2 | i.p. | >1600 |
| Example 3 | i.p. | >1600 |
| Example 4 | i.p. | >1600 |
| Example 5 | i.p. | >1600 |
| Example 6 | i.p. | >1600 |
| Example 7 | i.p. | >1600 |
| Example 8 | i.p. | >1600 |
| Example 9 | i.p. | >1600 |
| Nalidixic acid | i.p. | 600 |

In view of their good pharmacological properties, the derivatives of the general formula I are therefore capable of being used in human and/or veterinary medicine for the treatment of systemic or localized acute, chronic and recurring infections caused by Gram-positive and Gram-negative microorganisms sensitive to the products forming the subject of the present invention, in the gastrointestinal or urogenital tract, the respiratory system, the skin and the soft tissues, as well as neurological and odontostomatologic infections.

In human therapy, the proposed dose of the derivatives of the present invention is approximately between 400 and 1200 mg/day of an adult, for example administered in the form of tablets or gelatin capsules. However, this dosage can vary according to the severity of the complaint.

Two particular pharmaceutical forms of the derivatives according to the present invention are now indicated below by way of examples.

| Example of formulation per tablet | |
|---|---|
| 6-Fluoro-7-(pyrrol-1-yl)-1-(2-fluoroethyl)-1,4-dihydro-4-oxoquinoline-3-carboxylic acid | 0.400 g |
| Carboxymethylstarch | 0.018 g |
| Polyvinylpyrrolidone K29-32 | 0.030 g |
| Microcrystalline cellulose | 0.146 g |
| Colloidal silicon dioxide | 0.003 g |
| Magnesium stearate | 0.003 g |
| | 0.600 g |
| Example of formulation per gelatin capsule | |
| 6-Fluoro-7-(pyrrol-1-yl)-1-methylamino-1,4-dihydro-4-oxoquinoline-3-carboxylic acid | 0.400 g |
| Microcrystalline cellulose | 0.0356 g |
| Colloidal silicon dioxide | 0.0022 g |
| Magnesium stearate | 0.0022 g |
| | 0.440 g |

What is claimed is:

1. A 1-substituted compound of 6-fluoro-7-(pyrrol-1-yl)-1,4-dihydro-4-oxoquinoline-3-carboxylic acid according to formula I:

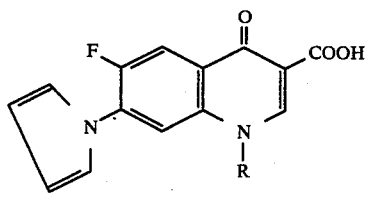

in which: R represents a methyl radical, a 2-hydroxyethyl radical, a vinyl radical, a cyclopropylmethyl radical, a propyl radical, a cyclopropyl radical, a 2-fluoroethyl radical, a methylamino radial or an ethylamino radical, as well as its physiologically acceptable alkali metal or alkaline earth metal salts.

2. 6-Fluoro-7-(pyrrol-1-yl)-1-methyl-1,4-dihydro-4-oxoquinoline-3-carboxylic acid corresponding to formula I as claimed in claim 1.

3. 6-Fluoro-7-(pyrrol-1-yl)-1-(2-hydroxyethyl)-1,4-dihydro-4-oxoquinoline-3-carboxylic acid corresponding to formula I as claimed in claim 1.

4. 6-Fluoro-7-(pyrrol-1-yl)-1-vinyl-1,4-dihydro-4-oxoquinoline-3-carboxylic acid corresponding to formula I as claimed in claim 1.

5. 6-Fluoro-7-(pyrrol-1-yl)-1-cyclopropylmethyl-1,4-dihydro-4-oxoquinoline-3-carboxylic acid corresponding to formula I as claimed in claim 1.

6. 6-Fluoro-7-(pyrrol-1-yl)-1-propyl-1,4-dihydro-4-oxoquinoline-3-carboxylic acid corresponding to formula I as claimed in claim 1.

7. 6-Fluoro-7-(pyrrol-1-yl)-1-(2-fluoroethyl)-1,4-dihydro-4-oxoquinoline-3-carboxylic acid corresponding to formula I as claimed in claim 1.

8. 6-Fluoro-7-(pyrrol-1-yl)-1-methylamino-1,4-dihydro-4-oxoquinoline-3-carboxylic acid corresponding to formula I as claimed in claim 1.

9. 6-Fluoro-7-(pyrrol-1-yl)-1-ethylamino-1,4-dihydro-4-oxoquinoline-3-carboxylic acid corresponding to formula I as claimed in claim 1.

10. 6-Fluoro-7-(pyrrol-1-yl)-1-cyclopropyl-1,4-dihydro-4-oxoquinoline-3-carboxylic acid corresponding to formula I as claimed in claim 1.

11. A pharmaceutical composition for use in human and veterinary medicine for the treatment of systemic or localized acute, chronic and recurring infections caused by Gram-positive and Gram-negative microorganisms, comprising:
   a pharmaceutically acceptable carrier; and
   a therapeutically active agent which includes a therapeutically effective amount of a compound as defined in claim 1.

12. An antibactrial composition, comprising an antibacterially therapeutically effective amount of a compound of formula I:

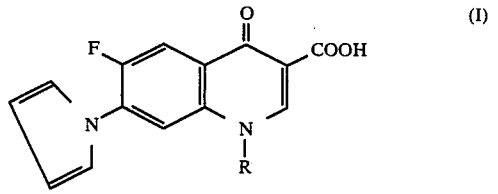

in which: R represents a methyl radical, a 2-hydroxyethyl radical, a vinyl radical, a cyclopropylmethyl radical, a propyl radical, a cyclopropyl radical, a 2-fluoroethyl radical, a methylamino radical or an ethylamino radical, as well as its physiologically acceptable alkali metal or alkaline earth metal salts; and a carrier.

13. A method of treating bacterial infections, comprising the steps of administering a therapeutically effective amount of a compound of the formula I.

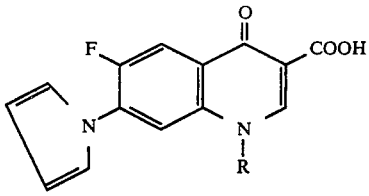

(I)

in which: R represents a methyl radical, a 2-hydroxyethyl radical, a vinyl radical, a cyclopropylmethyl radical, a propyl radical, a cyclopropyl radical, a 2-fluorethyl radical, a methylamino radical or an ethylamino radical, as well as its physiologically acceptable alkali metal or alkaline earth metal salts.

* * * * *

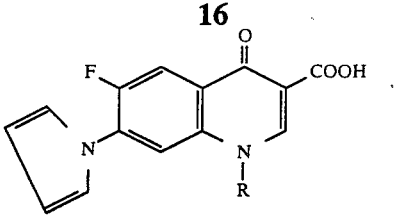

(I)

in which: R represents a methyl radical, a 2-hydroxyethyl radical, a vinyl radical, a cyclopropylmethyl radical, a propyl radical, a cyclopropyl radical, a 2-fluorethyl radical, a methylamino radical or an ethylamino radical, as well as its physiologically acceptable alkali metal or alkaline earth metal salts.

* * * * *

UNITED STATES PATENT OFFICE
CERTIFICATE OF CORRECTION

Patent No. 4,727,080                    Dated February 23, 1988

Inventor(s) Jose E. Soler

It is certified that error appears in the above-identified patent and that said Letters Patent are hereby corrected as shown below:

Column 3, line 15, delete "halide" and insert "halides".

Column 3, line 34, after "6-fluoro-7-", insert a parenthesis "(".

Column 3, line 36, delete "and" and insert "the".

Column 3, line 67, after "ethanol/", delete the hyphen "-".

Column 4, line 24, delete "wtih" and insert "with".

Column 4, line 43, delete "receystallized" and insert "recrystallized".

Column 4, line 69, delete "-caboxylate" and insert "carboxylate".

Column 5, line 35, delete "ml chloroform," and insert "ml of chloroform,".

Column 5, line 58, after ($J_{HF}$:6.3 $H_z$), 1" insert "H".

Column 6, line 1, delete "dimethlformamide" and insert "dimethylformamide".

Column 7, line 9, delete "-caboxylate," and insert "-carboxylate,"

Column 7, line 49, delete "for48" and insert "for 48".

Column 8, line 17, delete [d $J_{HF}$:" and insert "[d($J_{HF}$:".

Column 8, line 49, delete "acidifed" and insert "acidified".

Column 8, line 52, delete "ofa" and insert "of a".

Column 8, line 56, delete "1H19.02" and insert "1H]: 9.02".

UNITED STATES PATENT OFFICE
CERTIFICATE OF CORRECTION

Patent No. 4,727,080

Dated February 23, 1988

Inventor(s) Jose E. Soler

It is certified that error appears in the above-identified patent and that said Letters Patent are hereby corrected as shown below:

Column 9, line 4, delete "3,5-" and insert "2,5-".

Column 10, line 28, delete "Spectrscopic data:" and insert "Spectroscopic data:".

Column 10, line 49, delete "ATTC" and insert "ATCC".

Column 10, line 50, delete "ATTC" and insert "ATCC".

Column 10, line 58, delete "coil" and insert "coli".

Column 10, line 67, delete "ATTC" and insert "ATCC".

Columns 11-12, line 17, (Table 1), delete "concentrationa" and insert "concentrations".

Columns 11-12, line 17, (Table 1), delete "ginve" and insert "given".

Columns 11-12, under the column "Compound of example 1".

"delete "0.05 and insert "0.50".

UNITED STATES PATENT OFFICE
CERTIFICATE OF CORRECTION

Patent No. 4,727,080

Dated February 23, 1988

Inventor(s) Jose E. Soler

It is certified that error appears in the above-identified patent and that said Letters Patent are hereby corrected as shown below:

Columns 11-12, between line 59, under the column "MICROORGANISMS", delete "ATTC" and insert "ATCC".

Column 13, line 3, delete "as" and insert "are".

Column 13, line 46, delete "0.400 g".

Column 14, line 2, delete "radial" and insert "radical".

Column 14, line 47, delete "pount of formula I:" and insert "pound of the formula I:".

Column 14, line 67, delete "steps" and insert "step".

Column 14, line 68, delete "formula I." and insert "formula I:".

Signed and Sealed this

Eleventh Day of October, 1988

Attest:

DONALD J. QUIGG

Attesting Officer

Commissioner of Patents and Trademarks

UNITED STATES PATENT OFFICE
CERTIFICATE OF CORRECTION

Patent No. 4,727,080      Dated February 23, 1988

Inventor(s) Jose E. Soler

It is certified that error appears in the above-identified patent and that said Letters Patent are hereby corrected as shown below:

In the Bibliographical Information Section, under the "Notice", please delete "March 24, 2004" and insert --November 12, 2002--.

Signed and Sealed this

Twenty-fifth Day of October, 1988

*Attest:*

DONALD J. QUIGG

*Attesting Officer*      *Commissioner of Patents and Trademarks*